United States Patent [19]
Shaffer et al.

[11] 4,147,768
[45] Apr. 3, 1979

[54] ENTERIC COATED DIGOXIN AND THERAPEUTIC USE THEREOF

[75] Inventors: Richard D. Shaffer; John J. Windheuser, both of Lawrence, Kans.

[73] Assignee: Interx Research Corporation, Lawrence, Kans.

[21] Appl. No.: 907,489

[22] Filed: May 19, 1978

Related U.S. Application Data

[63] Continuation of Ser. No. 722,606, Sep. 13, 1976, abandoned.

[51] Int. Cl.$^2$ .......................... A61K 9/46; A61K 9/36; A61K 31/705
[52] U.S. Cl. ........................................ 424/35; 424/44; 424/182
[58] Field of Search ................................. 424/19–22, 424/32–38, 44, 182

[56] References Cited

U.S. PATENT DOCUMENTS

| | | | |
|---|---|---|---|
| 536,155 | 3/1895 | Noyes | 424/44 |
| 1,690,760 | 11/1928 | Volwiler | 424/35 |
| 2,196,768 | 4/1940 | Hiatt | 424/35 |
| 2,433,244 | 12/1947 | Springett | 424/35 |
| 2,540,979 | 2/1951 | Clymer et al. | 424/35 |
| 2,698,822 | 1/1955 | Halpern et al. | 424/182 |
| 2,887,440 | 5/1959 | Greminger et al. | 424/35 |
| 3,081,233 | 3/1963 | Enz et al. | 424/35 |
| 3,131,123 | 4/1964 | Masquelier | 424/44 |
| 3,939,259 | 2/1976 | Pescetti | 424/20 |
| 3,961,041 | 6/1976 | Nishimura et al. | 424/35 |

OTHER PUBLICATIONS

Svec, Chem. Abstr. 32 #5912(8) (1938).
Lingner et al.. Chem. Abstr. 57 #17317c (1962).
Sila, Chem. Abstr. 64 #9516f (1966).
Kasahara et al., Chem. Abstr. 72 #1897w (1970).
Kuhlemann et al., Chem. Abstr. 78 #148183t (1973).
Beermann et al., Chem. Abstr. 78 #67145e (1973).
Mentz et al., Arch. Int. Pharmacodyn 200:126–140 (1972) "Active or Passive Enteric Resorption of Cardiac Glycosides"(U.S.P.T.O. Transl.).

Primary Examiner—Shep K. Rose
Attorney, Agent, or Firm—Bacon & Thomas

[57] ABSTRACT

Therapeutic and undegraded levels of digoxin in warm-blooded animals are achieved by orally admininstering thereto, a non-toxic pharmaceutical enteric-coated tablet comprising:

(a) A cardiotonic effective amount of digoxin;
(b) a non-toxic pharmaceutically acceptable inert diluent, and
(c) a standard non-toxic pharmaceutically acceptable enteric coating.

This composition is extremely useful in the treatment of cardiac insufficiency in warm-blooded animals. When administered to warm-blooded animals (e.g., humans), superior therapeutic and undegraded blood levels of digoxin are observed over that normally observed with conventional solid dosage formulations for oral administration.

6 Claims, 2 Drawing Figures

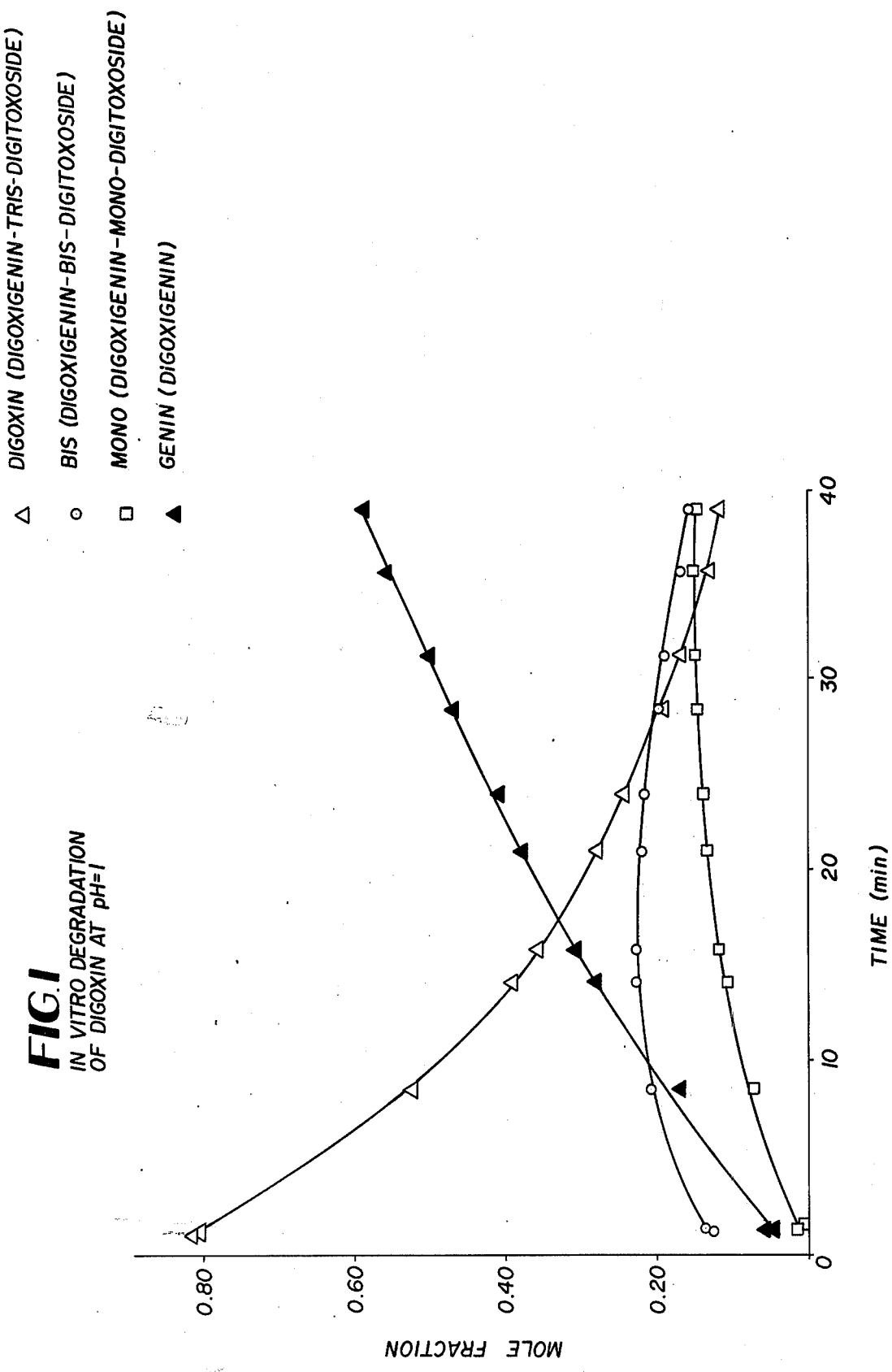

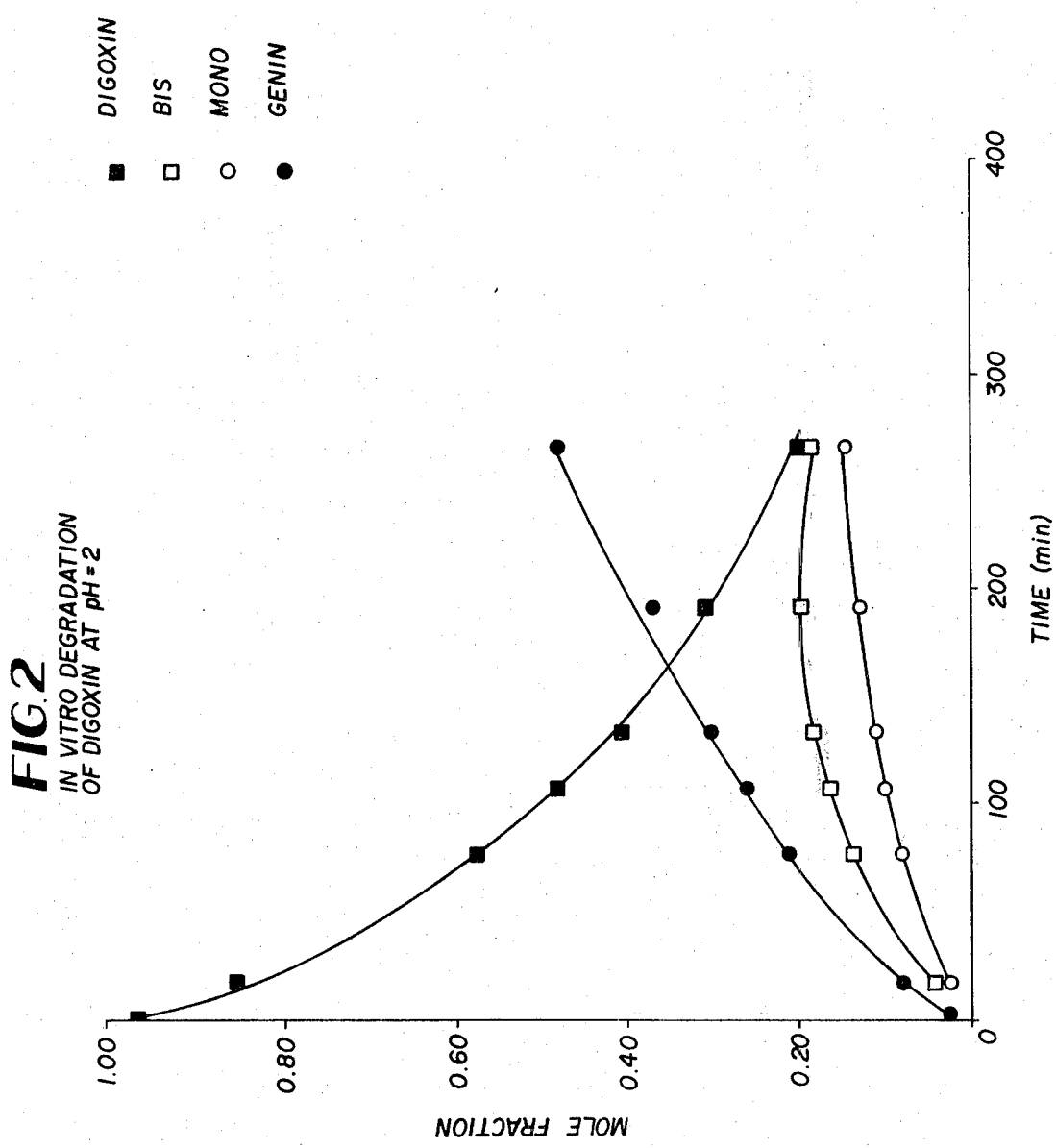

ENTERIC COATED DIGOXIN AND THERAPEUTIC USE THEREOF

This is a continuation of application Ser. No. 722,606, filed Sept. 13, 1976 now abandoned.

BACKGROUND OF THE INVENTION

1. Field of the Invention

The present invention is directed to digoxin and more particularly, a novel and unique solid dosage form for orally administering digoxin to warm-blooded animals, e.g., humans.

2. Description of the Prior Art

Digoxin is a cardiotonic drug, used in the field of medicine to achieve an increase in the force of myocardial contraction. Essentially, digoxin is a conduction system depressant which acts in such a manner as to decrease cardiac rate.

The structural formula for digoxin is set out below, and conventionally speaking, the dose administered to a patient (orally) to achieve digitalization is approximately 1.5 mg initially, and thereafter, a maintenance dose of approximately 0.5 mg is usually required.

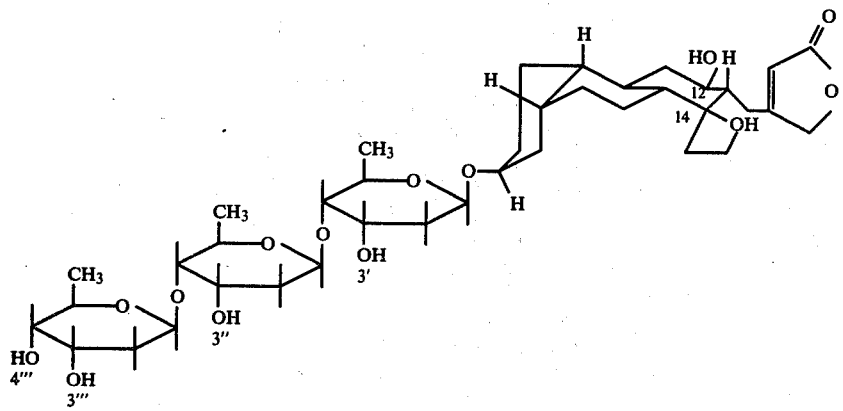

Digoxin is used in the treatment of cardiac failure, atrial fibrillation and flutter, paroxysinal tachycardia, cardiac insufficiency, etc. This compound has the advantage as compared to digitoxin, and that its onset of action is quite more rapid, and further, its duration of action is relatively shorter. This compound has an additional advantage in that in the event of an overdose, the symptoms associated therewith are more readily dissipated.

Recently, many articles have been published on the variation in the absorption of digoxin, administered via conventional oral solid dosage forms, e.g., tablets, capsules, etc. These variations in digoxin absorption have been noted in both inter- and intrapatient studies. While potential sources of digoxin variability from standard oral solid dosage form formulations and/or oral administration have been postulated and investigated, no real answer to the problem has been determined.

The digoxin molecule consists of a steroidal (digoxigenin) nucleus in glycosidic linkage with three sugar(-digitoxose) moieties. The present inventors have determined that each of these sugar moieties are prone to acid "cleavage" or hydrolysis under acidic conditions (synonymous with the acidic environment of the stomach, pH=1). Accordingly, the present inventors have further determined that conventional oral solid dosage formulations intended to deliver digoxin are inappropriate in that the drug in such formulations is subject to hydrolytic attack in the acid environment of the stomach, the result of which is a sequential cleavage of the three sugar moieties on the overall steroidal digoxin nucleus. As a consequence thereof, the delivery of therapeutic and undegraded levels of digoxin is greatly impeded.

In the past, numerous attempts at improving the solubility of digoxin via molecular modification have been made. See, U.S. Pat. No. 3,884,905. However, the present inventors believe their discovery is the first discovery specifically dealing with the inability of digoxin to be absorbed as the intact (undegraded) molecule. Very recently, it has been proposed to deliver digoxin via "soft" gelatin capsules. While such approach might aid in the basic delivery of digoxin, such approach does not solve the degradation phenomenon discussed earlier due to the fact that the drug in soft gelatin capsules is subject to attack in the acidic environment of the stomach.

SUMMARY OF THE INVENTION

In view of the foregoing, it is obviously apparent that a great need exists for a solid oral dosage form for administering digoxin which form will not be subject to attack by the acidic environment of the stomach but rather render itself subject to attack in the basic environment of the intestine.

Accordingly, the foregoing degradation phenomenon associated with digoxin is eliminated when digoxin is administered to a warm-blooded animal in the form of an enteric-coated formulation for oral delivery. Specifically, the present invention contemplates an enteric-coated formulation consisting essentially of a tableted admixture of the following:

(a) a cardiotonic effective amount of digoxin, and (b) a non-toxic pharmaceutically acceptable inert diluent; and (c) a standard non-toxic pharmaceutically acceptable enteric coating maintained over said tableted mixture of (a) and (b) above.

DETAILED DESCRIPTION OF THE INVENTION

The term "digoxin" as used herein is meant to include digoxin per se or any digoxin derivative capable of reverting to digoxin in vivo. Suitable but nonlimiting examples of such derivatives are found in U.S. Pat. Nos. 3,839,317, 3,884,905 and 3,929,996 and U.S. patent application, Ser. No. 664,687, filed Mar. 8, 1976, the subject matter of which is incorporated herein by reference. Additionally, it is obviously apparent that other chemically related cardiac glycosides can be substituted for digoxin. Illustrative are digitoxin, gitoxin, lanatoside C, deslanoside, strophanthin, etc..

The non-toxic pharmaceutically acceptable inert diluent can be selected from among any one of a number of diluents familiar to those skilled in the art. However, without limitation, the following are illustrative: lactose, starch (pharmaceutical grade), dicalcium phosphate, calcium sulfate, kaolin, mannitol and powdered sugar. Additionally, when required, suitable binders, lubricants and disintegrating agents can be added as well. Typical binders include starch, gelatin, sugars, such as sucrose, molasses and lactose, natural and synthetic gums, such as acacia, sodium alginate, extract of Irish Moss, carboxymethylcellulose, methylcellulose and polyvinylpyrrolidone, polyethylene glycol, ethylcellulose and waxes. Typical lubricants include, without limitation, boric acid, sodium benzoate, sodium acetate, sodium chloride, leucine and polyethylene glycol. Finally, suitable disintegrators can include, without limitation, starch, methylcellulose, agar, bentonite, cellulose and wood products, alginic acid, guar gum, citris pulp, carboxymethylcellulose and sodium lauryl sulfate.

As for the non-toxic pharmaceutically acceptable enteric coating, any one of a number of conventional enteric coatings can be employed. For example, without limitation, cellulose acetate phthalate (CAP) and hydroxypropylmethyl cellulose phthalate (HPMCP), etc. are suitable. Ohter enteric coatings suitable for the purpose of the instant invention can be found in the text entitled "REMINGTON'S PHARMACEUTICAL SCIENCES," Fourteenth Edition (1970), pgs. 1689–1691. Specifically preferred enteric coatings are HPMCP-50 and HPMCP-45, respectively.

In a most preferred embodiment, an effervescent enteric-coated formulation as described in U.S. Pat. No. 3,961,041 is desirable. This formulation is essentially identical to that described above with the exception that a carbon dioxide releasing non-toxic pharmaceutically acceptable effervescent couple acid (e.g., tartaric acid, citric acid, citric anhydride, etc.) and base (sodium bicarbonate, sodium carbonate, etc.) are added to the formulation. Upon contact of the effervescent enteric-coated preparation with the intestinal juice, effervescence rapidly occurs, thus causing total disintegration and release of digoxin all at once. For purposes of this application, the subject matter of U.S. Pat. No. 3,961,041, noted earlier, is incorporated herein by reference.

Without further elaboration, it is believed that one of ordinary skill in the art can, using the preceding description, utilize the present invention to its fullest extent. As such, the following preferred specific embodiments are, therefore, to be construed as merely illustrative and not limitative of the remainder of the specification and claims in any way whatsoever.

EXAMPLE I

A sample amount of pharmaceutical grade digoxin was introduced into two solutions, one being a 0.1 N hydrochloric acid solution (pH=1) and the other being a solution comprising a mixture of 0.01 N hydrochloric acid and 0.09 N sodium chloride (pH=2). The cleavage or degradation of digoxin from each solution was measured under High Pressure Liquid Chromatography (HPLC). The chromatography was performed on a component system consisting of a Waters M6000A solvent delivery system and a U6K universal injector coupled with a Varian Vari-chrom detector, operated at 225 nm. The separation utilized a Waters $\mu$ Bondapak C18 column (4 nm×30 cm), operating at 2.0 ml/min with a methanol/water (55:45) mobile phase. Retention volumes were digoxigenin; 4.4 ml, mono; 4.2 ml, bis; 8.2 ml, and digoxin; 12.8 ml.

In FIGS. 1 and 2 accompanying the present application, there is shown the degradation or cleavage rates for digoxin from the above-identified solutions. As can be easily observed, at a pH of 1, digoxin is rapidly degraded to the final "genin" degradation product, digoxigenin. At a pH of 2, the cleavage or degradation of digoxin is much less rapid.

To complete the study, buffered solutions at pH 4 (citrate buffer) and pH 7 (trishydroxymethyl ammonia buffer) were prepared. A digoxin sample was introduced into each solution after which cleavage (degradation) of the compound was observed. The cleavage (degradation) rate was so slow that it could not be followed by HPLC.

The foregoing studies and results gained therefrom clearly demonstrate that at low pH, equivalent to that observed in the stomach of warm-blooded animals (pH=1), digoxin is rapidly degraded to its non-glycoside form, i.e., genin (digoxigenin). It has further been shown that as the pH is elevated to that synonymous with that maintained in the intestinal tract (pH=4, pH=7), degradation of digoxin to its bis (digoxigenin-bis-digitoxoside), mono (digoxigenin-mono-digitoxoside) and genin (digoxigenin) forms is not observed.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably and intended to be, within the full range of equivalents of the following claims.

What we claim is:

1. A pharmaceutically acceptable enteric coated tablet for orally delivering therapeutic and undegraded levels of digoxin to a warm-blooded animal which comprises an admixture of:
    (a) a cardiotonic effective amount of digoxin;
    (b) a non-toxic pharmaceutically acceptable inert diluent;
    (c) a non-toxic pharmaceutically acceptable effervescent couple-acid and base; and
    (d) a standard non-toxic pharmaceutically acceptable enteric coating maintained over said tableted mixture of (a), (b) and (c) above.

2. The tablet of claim 1, wherein said enteric coating is a member selected from the group consisting of cellulose acetate phthalate and hydroxypropylmethylcellulose phthalate.

3. The tablet of claim 2, wherein said hydroxypropylmethylcellulose phthalate is a member selected from the group consisting of hydroxypropylmethylcellulose phthalate-45 and hydroxypropylmethylcellulose phthalate-50.

4. A method for inducing therapeutic and undegraded levels of digoxin in a warm-blooded animal which comprises administering thereto, a pharmaceutically acceptable enteric coated tablet comprising an admixture of:

(a) a cardiotonic effective amount of digoxin;
(b) a non-toxic pharmaceutically acceptable inert diluent;
(c) a non-toxic pharmaceutically acceptable effervescent couple-acid and base; and
(d) a non-toxic pharmaceutically acceptable enteric coating maintained over said tableted mixture of (a), (b) and (c) above.

5. The method of claim 4, wherein said enteric coating is a member selected from the group consisting of cellulose acetate phthalate and hydroxypropylmethylcellulose phthalate.

6. The method of claim 5, wherein said hydroxypropylmethylcellulose phthalate is a member selected from the group consisting of hydroxypropylmethylcellulose phthalate and hydroxypropylmethylcellulose phthalate-50.

* * * * *